United States Patent [19]

Kadokawa et al.

[11] Patent Number: 4,677,107

[45] Date of Patent: Jun. 30, 1987

[54] ANTI-PEPTIC ULCER AGENT

[75] Inventors: Toshiaki Kadokawa, Hirakata; Katsuyoshi Kawashima, Kobe; Hitoshi Uno, Takatsuki; Katsuhiko Hino, Nara, all of Japan

[73] Assignee: Dainippon Pharmaceutical Co., Ltd., Japan

[21] Appl. No.: 784,215

[22] Filed: Oct. 4, 1985

Related U.S. Application Data

[63] Continuation-in-part of Ser. No. 613,501, May 23, 1984, abandoned.

[30] Foreign Application Priority Data

May 31, 1983 [JP]  Japan .................................. 58-97523
Oct. 9, 1984 [JP]  Japan ................................ 59-212197

[51] Int. Cl.⁴ ............................................ A61K 1/495
[52] U.S. Cl. ................... 514/254; 514/926; 514/927
[58] Field of Search .................... 514/254, 926, 927

[56] References Cited

U.S. PATENT DOCUMENTS 4,237,135  12/1980  Uno et al. ........................ 514/254

*Primary Examiner*—Frederick E. Waddell

*Attorney, Agent, or Firm*—Scully, Scott, Murphy & Presser

[57] ABSTRACT

Use of a compound of the formula:

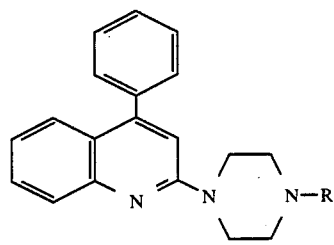

wherein R is hydrogen atom or ethyl group, or a pharmaceutically acceptable salt thereof for prophylaxis and/or treatment of peptic ulcer, and a method for prophylaxis and/or treatment of peptic ulcer disease which comprises administering an effective amount of the above-mentioned compound to warm blooded animal, especially human. Said active compounds have excellent pharmacological activities such as inhibition of ulceration and inhibition of gastric secretion, and hence, are useful as an anti-peptic ulcer agent.

11 Claims, 1 Drawing Figure

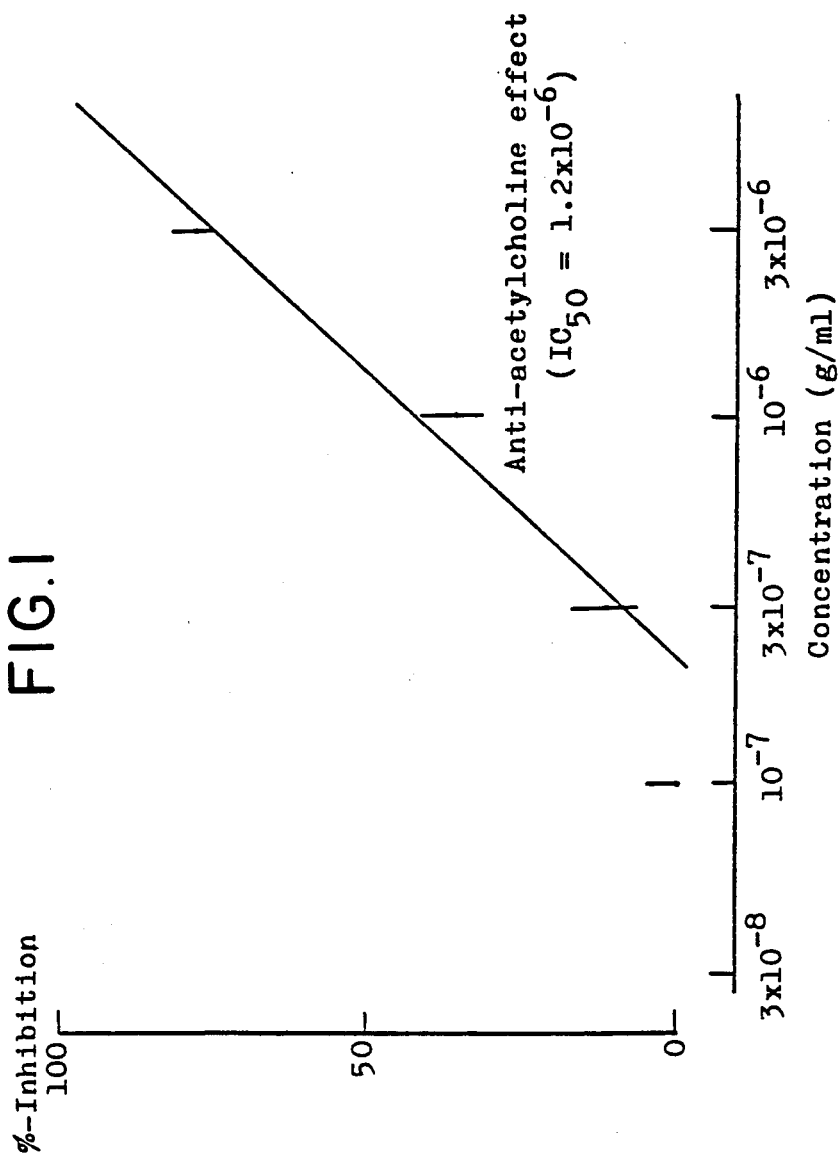

ANTI-PEPTIC ULCER AGENT

This is a continuation-in-part application of U.S. patent application Ser. No. 613,501 filed on May 23, 1984, now abandoned.

The present invention relates to an anti-peptic ulcer agent. More particularly, it relates to use of 2-(4-ethyl-1-piperazinyl)- or 2-(1-piperazinyl)-4-phenylquinoline or a pharmaceutically acceptable salt thereof for prophylaxis and/or treatment of peptic ulcer, and a method for prophylaxis and/or treatment of peptic ulcer disease which comprises administering an effective amount of the abovementioned compound to warm blooded animal, especially human.

The 2-(4-ethyl-1-piperazinyl)- or 2-(1-piperazinyl)-4-phenylquinoline (occasionally referred to "present compound") is shown by the following chemical structure:

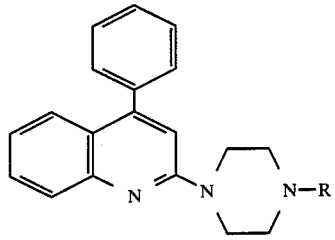

[I]

wherein R is hydrogen atom or ethyl group.

The pharmaceutically acceptable salts of the present compounds [I] include salts with inorganic acids such as hydrochloric acid, hydrobromic acid, hydroiodic acid, sulfuric acid, phosphoric acid, and organic acids such as citric acid, maleic acid, fumaric acid, tartaric acid, benzoic acid, lactic acid, methanesulfonic acid. Preferred salts are monomaleate, dimaleate and dihydrochloride, and particularly preferred salts are monomaleate and dimaleate. These salts may occasionally be present in the form of hydrates, and hence, the active compounds of the present invention include also such hydrates.

It is disclosed in U.S. Pat. No. 4,237,135 and U.K. Pat. No. 2,017,698 etc. that 2-(4-ethyl-1-piperazinyl)-4-phenylquinoline and some analogous compounds were evaluated on some pharmacological activities from the viewpoint of antidepressant, and showed anti-reserpine activity, anti-tetrabenazine activity, suppression of mouse-killing behavior of olfactory bulb-ablated rats, inhibition of brain noradrenaline turnover, etc., and therefore, are useful as an antidepressant agent. It is disclosed in the above patents that 2-(4-ethyl-1-piperazinyl)-4-phenylquinoline has also anti-tremorine activity and hence is also useful as an antiparkinsonian agent. It is also disclosed in the patents that 2-(1-piperazinyl)-4-phenylquinoline is useful as an intermediate for preparing the active compounds.

On the other hand, it is also disclosed in U.S. Pat. No. 3,542,785 and 3,668,207 that some phenylquinoline compounds including 6-chloro-2-(4-methyl-1-piperazinyl)-4-phenylquinoline and 6-chloro-2-(4-phenyl-1-piperazinyl)-4-phenylquinoline have anti-inflammatory activity and diuretic activity. It is disclosed in U.S. Pat. No. 4,237,135 and U.K. Pat. No. 2,017,698 that the above 6-chloro-2-(4-methyl-1-piperazinyl)-4-phenylquinoline possesses also weak anti-reserpine activity.

Moreover, it is disclosed in Chem. Pharm. Bull., 28 (9), 2618-2622 (1980) that a series of 2-amino-4-phenylquinolines including the present compounds have antidepressant activity, wherein there is also disclosed synthesis of these compounds.

It has now unexpectedly been found that the active compounds of the present invention have anti-peptic ulcer activity.

The active compounds of the present invention show excellent pharmacological activities supporting usefulness as an anti-peptic ulcer agent, and the activities are greater than those of some commercially available anti-ulcer agents. Moreover, the active compounds of the present invention hardly show undesirable side effects such as mydriasis. Accordingly, the active compounds of the present invention are useful for prophylaxis and/or treatment of peptic ulcer disease.

The pharmacological activities of the active compounds of the present invention, especially those of 2-(4-ethyl-1-piperazinyl)-4-phenylquinoline dihydrochloride (hereinafter, occasionally referred to as "Compound A"), 2-(4-ethyl-1-piperazinyl)-4-phenylquinoline dimaleate (hereinafter, occasionally referred to as "Compound B") and 2-(1-piperazinyl)-4-phenylquinoline monomaleate (hereinafter, occasionally referred to as "Compound C") are described in detail hereinbelow.

[I] Effect on the ulceration induced by exposure to stress (restraint and water immersion):

Male Wistar strain rats (weighing, about 200 g) were placed in a stress cage which served to immobilize the animals therein and then immersed in a water bath of 23° C. to the height of xiphoid of the animals according to the method of Takagi et al. [cf. Takagi, K. and Okabe, S., Japan. J. Pharmacol., 18, 9 (1968)]. After 20 hours, the animals were sacrificed and the stomach was removed. The stomach was inflated with 13 ml of saline and placed in 5% formalin solution for 5 minutes. After washing with saline, the stomach was cut open along the greater curvature and the length (mm) of each lesion in the glandular portion was measured using a dissecting microscope (×12). The sum of the length (mm) of each lesions in a stomach was indicated as an ulcer index. In case of reference experiment using butylscopolamine bromide, a photograph of the mucosal surface of stomach was taken after the stomach was treated in the same manner as described above. The photograph was magnified by nine times, and the sum of the area ($mm^2$) of each lesions in a stomach was indicated as an ulcer index. The ulcer index in drug treated groups was compared with that in control group, and thereby, inhibitory percentage was calculated and then $ED_{50}$ value, i.e., the dose required for 50% inhibition of the ulcer index, was determined by the usual graphic method. Drugs to be tested were suspended in 0.5% tragacanth solution and administered orally 30 minutes before the immersion. In the control group, a vehicle (0.5% tragacanth solution) was administered. The results are shown in Table 1.

TABLE 1

| Test drugs | Dose (mg/kg, p.o.) | Number of animal | Ulcer index Inhibitory % | $ED_{50}$ (mg/kg) |
|---|---|---|---|---|
| Control | — | 5 | — | 2.8 |
| Compound A | 1 | 5 | 15.5 | |
| | 2 | 5 | 40.8 | |
| | 5 | 5 | 85.2 | |
| | 10 | 5 | 88.4 | |
| Control | — | 5 | — | 1.2 |

TABLE 1-continued

| Test drugs | Dose (mg/kg, p.o.) | Number of animal | Ulcer index Inhibitory % | $ED_{50}$ (mg/kg) |
|---|---|---|---|---|
| Compound B | 1 | 5 | 44.5 | |
| | 2 | 5 | 66.6 | |
| | 5 | 5 | 90.1 | |
| Control | — | 5 | — | 0.45 |
| Compound C | 0.2 | 5 | 45.8 | |
| | 0.5 | 5 | 55.5 | |
| | 1 | 5 | 55.9 | |
| | 2 | 5 | 73.6 | |
| | 5 | 5 | 71.8 | |
| Control | — | 5 | — | 26.9 |
| Cimetidine (reference) | 20 | 5 | 29.1 | |
| | 50 | 5 | 75.0 | |
| | 100 | 5 | 77.0 | |
| Control | — | 14 | — | 49.1 |
| Butyl-scopolamine bromide (reference) | 20 | 10 | −2.1 | |
| | 50 | 9 | 44.1 | |
| | 100 | 12 | 97.8 | |

[II] Effect on the ulceration induced by pylorus-ligation in rats:

Male Wistar strain rats (weighing about 190 g) were fasted for 48 hours before experiment. The pylorus of each rat was ligated under ether anaesthesia according to the method of Shay et al. [cf. Shay, H., et al., Gastroenterology, 5, 43–61 (1945)]. Each of the animals was then allowed to stand abstained from food and water in a cage. After 18 hours, the animals were sacrificed under ether anaesthesia, and the stomachs were removed and cut open along the greater curvature. The state of ulceration was observed with naked eyes and degree of ulceration was estimated according to the ulcer index 0 to 5 as follows:

0: no lesion
1: hemorrage or erosion
2: one to five small ulcers (diameter, less than 5 mm)
3: many small ulcers more than five or one marked ulcer of a diameter of more than 5 mm
4: marked ulcers more than two
5: perforated ulcer The ulcer index in drug treated groups was compared to that in the control group, and thereby, the inhibitory percentage was calculated and then $ED_{50}$, i.e. the dose required for 50% inhibition of ulcer index, was determined by the usual graphic method. Drugs to be tested were suspended in 0.5% tragacanth solution and administered 30 minutes before the ligation. In the control group, a vehicle (0.5% tragacanth solution) was administered. The results are shown in Table 2.

TABLE 2

| Test drugs | Dose (mg/kg, p.o.) | Number of animal | Ulcer index Inhibitory % | $ED_{50}$ (mg/kg) |
|---|---|---|---|---|
| Control | — | 5 | — | 16 |
| Compound A | 5 | 5 | 35.3 | |
| | 10 | 5 | 41.2 | |
| | 20 | 5 | 52.9 | |
| | 50 | 5 | 76.5 | |
| Control | — | 5 | — | 19 |
| Compound B | 5 | 5 | 0 | |
| | 10 | 5 | 28.6 | |
| | 20 | 5 | 57.1 | |
| | 50 | 5 | 78.6 | |
| Control | — | 5 | — | 14 |
| Compound C | 5 | 4 | 37.5 | |
| | 10 | 5 | 43.8 | |
| | 20 | 5 | 56.3 | |
| | 50 | 5 | 75.0 | |
| Control | — | 9 | — | 253 |

TABLE 2-continued

| Test drugs | Dose (mg/kg, p.o.) | Number of animal | Ulcer index Inhibitory % | $ED_{50}$ (mg/kg) |
|---|---|---|---|---|
| Cimetidine (reference) | 50 | 9 | 0 | |
| | 100 | 10 | 9.1 | |
| | 200 | 9 | 42.4 | |
| | 500 | 5 | 75.8 | >200 |
| Control | — | 5 | — | |
| Butyl-scopolamine bromide (reference) | 50 | 5 | 19.0 | |
| | 100 | 5 | 28.6 | |
| | 200 | 5 | 38.1 | |

[III] Effect on gastric secretion in rats:

Male Wistar strain rats (weighing, about 200 g) were fasted for 24 hours before experiment. The pylorus was ligated under ether anaesthesia. Four hours after the ligation, the stomach was removed under ether anaesthesia. The gastric content was collected and centrifuged, and the secretory volume, pH and acid content of the supernatant were measured. The acid content was measured by titrating to pH 7.0 with 0.02N NaOH using pH meter (Hitachi Horiba, M-5). The total acid content of the drug treated groups was compared with that of the control group, and thereby, the reduction percentage of acid content was calculated and then $ED_{50}$, i.e. the dose required for 50% reduction of acid content, was determined by the usual graphic method. Drugs to be tested were suspended in 0.5% tragacanth solution and administered orally 30 minutes before the ligation. In the control group, a vehicle (0.5% tragacanth solution) was administered. The results are shown in Table 3.

TABLE 3

| Test drugs | Dose (mg/kg, p.o.) | Number of animal | Total acid content Reduction % | $ED_{50}$ (mg/kg) |
|---|---|---|---|---|
| Control | — | 5 | — | 1.8 |
| Compound A | 0.5 | 5 | 18.2 | |
| | 1 | 5 | 34.7 | |
| | 2 | 5 | 54.5 | |
| | 5 | 5 | 73.1 | |
| Control | — | 5 | — | 2.8 |
| Compound B | 0.5 | 5 | 27.8 | |
| | 1 | 5 | 24.0 | |
| | 2 | 5 | 47.8 | |
| | 5 | 5 | 60.2 | |
| Control | — | 5 | — | 1.1 |
| Compound C | 1 | 5 | 45.3 | |
| | 2 | 5 | 71.3 | |
| | 5 | 5 | 86.3 | |
| Control | — | 5 | — | 26.8 |
| Cimetidine (reference) | 10 | 5 | 9.4 | |
| | 20 | 5 | 44.0 | |
| | 50 | 5 | 71.6 | |
| Control | — | 5 | — | 25.0 |
| Butyl-scopolamine bromide (reference) | 20 | 5 | 44.3 | |
| | 50 | 5 | 71.0 | |
| | 100 | 4 | 83.7 | |
| (reference) | | | | |

[IV] Mydriatic action in rats:

Male Wistar strain rats (weighing, 150–200 g) were used. Pupil size of the animals was twice measured microscopically just before and one hour after administration of drugs at a distance of 30 cm from the source of a constant light (30 W fluorescent light) according to the method of Pulewka [cf. Arch. exp. Path. U. Pharmakol., 168, 307 (1932)]. Based on the change between the first measured pupil size and the second measured pupil size, mydriasis percentage was calculated provided that mydriasis percentage is supposed to be 100 percent in case of 3 mm dilation of pupil size in diameter. Drugs to be tested were suspended in 0.5% tragacanth solution and administered. In the control group, a vehicle (0.5% tragacanth solution) was administered. The results are shown in Table 4. As is clear from the results, Compounds A and B did entirely not show any mydriatic action even in a dose of 100 mg/kg.

TABLE 4

| Test drugs | Dose (mg/kg, p.o.) | Number of animal | Percent mydriasis |
| --- | --- | --- | --- |
| Control | — | 5 | −1.3 |
| Compound A | 5 | 5 | 4.0 |
| | 10 | 5 | 2.7 |
| | 20 | 5 | 2.7 |
| | 50 | 5 | 1.3 |
| | 100 | 5 | 2.6 |
| Control | — | 5 | −2.0 |
| Compound B | 5 | 5 | 0 |
| | 10 | 5 | 2.7 |
| | 20 | 5 | 4.7 |
| | 50 | 5 | 2.0 |
| | 100 | 5 | 2.7 |

[IV] Anti-acetylcholine action:

A piece of ileum, taken from male Hartley guinea-pigs (weighing 250–350 g) was suspended longitudinally in a bath containing Tyrode solution (20 ml) under constant bubbling of 95% oxygen and 5% carbon dioxide gas at 35° C. The contraction of the preparation by acetylcholine chloride ($2 \times 10^{-8}$ g/ml) was recorded on an oscillograph (Nihonkoden, RJG-3004) via an isotonic transducer (Nihonkoden, TD-111S). Drugs to be tested (Compound A and Compound C) were added to the bath 2 minutes prior to the application of acetylcholine chloride. The average percent inhibition of the test Compound A against the contraction of ileum preparation by acetylcholine is shown in the accompanying FIG. 1. Based on the average percent inhibition on the graph, $IC_{50}$, i.e. 50% inhibition concentration of the test compound, was calculated. As a result, $IC_{50}$ of Compound A was $1.2 \times 10^{-6}$ g/ml. $IC_{50}$ of Compound C was calculated likewise. As a result, it was $1.9 \times 10^{-6}$ g/ml. Accordingly, anti-acetylcholine activity of Compound A and Compound C is extremely weak.

Further, the toxicological study was conducted according to the conventional method on Compound B. The results are shown in Table 5.

TABLE 5

| | $LD_{50}$(mg/kg. p.o.) | |
| --- | --- | --- |
| | Mouse (ICR strain) | Rat (SD strain) |
| Compound B | ca 1,200 | ca 3,600 |

As is clear from the above experimental results, the active compounds of the present invention show excellent pharmacological activities such as inhibition of ulceration and inhibition of gastric secretion in a low dose and show little or extremely low mydriatic action and low toxicity, and hence, are useful as an anti-peptic ulcer agent. When 2-(4-ethyl-1-piperazinyl)-4-phenylquinoline is orally administered, it is partially converted into 2-(1-piperazinyl)-4-phenylquinoline. Both compounds show the activity as mentioned above within the body.

The active compounds of the present invention can be administered in oral, parenteral or rectal route, but preferably in oral route. The dose of these compounds varies with the administration routes, age of the patients, severity of the disease to be treated, or the like, but are in the range of 0.01 to 20 mg/kg/day, preferably 0.1 to 2 mg/kg/day, (as the free base) for humans. The dose may be divided and administered in two to four times per day.

The active compounds of the present invention are usually used in the form of a pharmaceutical composition which contains the active compound in an effective and nontoxic amount in admixture with conventional pharmaceutical carriers suitable for oral, parenteral or rectal application and unreactive with the active compounds of the present invention. Suitable examples of the carriers are gelatine, lactose, sucrose, titanium oxide, starches, crystalline cellulose, sodium carboxymethyl cellulose, calcium carboxymethyl cellulose, hydroxypropyl cellulose, hydroxypropyl methyl cellulose, methyl cellulose, sorbitol, sorbitan fatty acid esters, polyvinylpyrrolidone, magnesium stearate, light anhydrous silicic acid, talc, vegetable oils, benzyl alcohol, gum arabic, propylene glycol, polyalkylene glycol, or the like. The pharmaceutical composition may be in the dosage form of solid preparations such as tablets, capsules, granules, fine granules, powders, suppositories, or liquid preparations such as syrups, elixir, injections, or the like. These preparations can be prepared by conventional methods. Liquid preparations may be prepared by dissolving or suspending the active compound of the present invention in water or other suitable vehicles, when used. Tablets and granules may be coated in a conventional manner. For injection, the preparation may be prepared by dissolving a pharmaceutically acceptable acid addition salt of the present compound in distilled water for injection, if necessary, followed by making isotonic with isotonic agents such as glucose, saline, or the like, and further, other ingredients such as pH adjusting agents and preservatives may be admixed thereto. These pharmaceutical compositions contain usually as the active ingredient the active compound of the present invention in the ratio of 0.5% by weight or more, preferably 1 to 60% by weight, based upon the whole weight of the compositions. The compositions may also contain one or more other therapeutically active compounds.

The present invention is illustrated by the following Examples for preparing pharmaceutical preparations and for synthesis of the active compounds of the present invention, but should not be construed to be limited thereto.

EXAMPLE 1

| Ingredients | Weight per 1,000 tablets |
| --- | --- |
| 2-(4-Ethyl-1-piperazinyl)-4-phenylquinoline dihydrochloride | 5 g |
| Corn starch | 33 g |
| Lactose | 75 g |
| Microcrystalline cellulose | 30 g |
| Hydroxyproyl cellulose | 5 g |
| Light anhydrous silicic acid | 1 g |
| Magnesium stearate | 1 g |

The above ingredients were kneaded, granulated and made into 1,000 tablets each weighing 150 mg by a conventional method. The tablets were further coated with hydroxypropyl methyl cellulose, talc, titanium dioxide, and sorbitan fatty acid ester in a customary manner. There were obtained 1,000 film coated tablets.

EXAMPLE 2

| Ingredients | Weight per 1,000 capsules |
| --- | --- |
| 2-(4-Ethyl-1-piperazinyl)-4-phenylquinoline dihydrochloride | 10 g |
| Corn starch | 49 g |
| Lactose | 15 g |
| Microcrystalline cellulose | 25 g |
| Talc | 0.5 g |
| Magnesium stearate | 0.5 g |

The above ingredients were kneaded, granulated and filled into 1,000 capsules by a conventional method.

EXAMPLE 3

| Ingredients | Weight per 1,000 tablets |
| --- | --- |
| 2-(4-Ethyl-1-piperazinyl)-4-phenylquinoline dihydrochloride | 25 g |
| Corn starch | 34 g |
| Lactose | 80 g |
| Microcrystalline cellulose | 53 g |
| Polyvinylpyrrolidone | 6 g |
| Light anhydrous silicic acid | 1 g |
| Magnesium stearate | 1 g |

The above ingredients were kneaded, granulated and made into 1,000 tablets each weighing 200 mg by a conventional method. The tablets were further coated in a similar manner as described in Example 1.

EXAMPLE 4

| Ingredients | Weight |
| --- | --- |
| 2-(4-Ethyl-1-piperazinyl)-4-phenylquinoline dimaleate | 10 g |
| Lactose | 395 g |
| Corn starch | 75 g |
| Hydroxypropyl methyl cellulose | 20 g |

The above ingredients were mixed with distilled water, kneaded, granulated by passing through a screen (24 mesh), and dried to give granules.

EXAMPLE 5

| Ingredients | Weight per 1,000 tablets |
| --- | --- |
| 2-(1-Piperazinyl)-4-phenylquinoline monomaleate | 5 g |
| Corn starch | 33 g |
| Lactose | 75 g |
| Microcrystalline cellulose | 30 g |
| Hydroxypropyl cellulose | 5 g |
| Light anhydrous silicic acid | 1 g |
| Magnesium stearate | 1 g |

The above ingredients were kneaded, granulated and made into 1,000 tablets each weighing 150 mg by a conventional method. The tablets were further coated with hydoxypropyl methyl cellulose, talc, titanium dioxide, and sorbitan fatty acid ester in a customary manner. There were obtained 1,000 film coated tablets.

EXAMPLE 6

| Ingredients | Weight per 1,000 tablets |
| --- | --- |
| 2-(1-Piperazinyl)-4-phenylquinoline monomaleate | 10 g |
| Corn starch | 49 g |
| Lactose | 15 g |
| Microcrystalline cellulose | 25 g |
| Talc | 0.5 g |
| Magnesium stearate | 0.5 g |

The above ingredients were kneaded, granulated and filled into 1,000 capsules by a conventional method.

EXAMPLE 7

Preparation of 2-(4-ethyl-1-piperazinyl)-4-phenylquinoline:

A solution of 2-chloro-4-phenylquinoline (2.0 g) and 1-ethylpiperazine (2.7 g) in toluene (15 ml) is heated under reflux for 10 hours. To the reaction mixture is added water and the resulting mixture is extracted with ethyl acetate. The extracts are dried over anhydrous sodium sulfate and concentrated under reduced pressure. The residue is chromatographed on silica gel (25 g) using chloroform as an eluent. Fractions containing the title compound are pooled and concentrated to give the title compound (2.3 g).

The free base thus obtained is treated with ethanolic hydrogen chloride to give the dihydrochloride of the title compound. Recrystallization from ethanol gives the pure dihydrochloride, m.p. 225°–230° C.

EXAMPLE 8

2-(4-Ethyl-1-piperazinyl)-4-phenylquinoline obtained in Example 7 is treated with a solution of maleic acid in ethanol to give 2-(4-ethyl-1-piperazinyl)-4-phenylquinoline dimaleate, m.p. 189°–190° C. (recrystallized from water-acetone).

EXAMPLE 9

In the same manner as described in Example 8 except that various acids are used instead of maleic acid, the following various salts are obtained.

2-(4-Ethyl-1-piperazinyl)-4-phenylquinoline difumarate, m.p. 183°–184° C. (recrystallized from methanol-ethyl acetate)

2-(4-Ethyl-1-piperazinyl)-4-phenylquinoline citrate, m.p. 182°–183° C. (recrystallized from water-ethanol)

2-(4-Ethyl-1-piperazinyl)-4-phenylquinoline ditartrate, m.p. 167°–168° C. (recrystallized from water-ethanol)

EXAMPLE 10

Preparation of 2-(1-piperazinyl)-4-phenylquinoline:

A solution of 2-chloro-4-phenylquinoline (4.0 g) and anhydrous piperazine (8.0 g) in toluene (4 ml) is heated under reflux for 5 hours. To the reaction mixture is added water and the resulting mixture is extracted with ethyl acetate. The extracts are dried over anhydrous sodium sulfate and concentrated under reduced pressure. The residue is chromatographed on silica gel (40 g) using chloroform as an eluent. Fractions containing the title compound are pooled and concentrated to give the title compound (4.4 g), m.p. 133°–134° C.

EXAMPLE 11

2-(1-Piperazinyl)-4-phenylquinoline obtained in Example 10 is treated with a solution of maleic acid in ethyl acetate to give 2-(1-piperazinyl)-4-phenylquinoline monomaleate, m.p. 187°–188° C. (recrystallized from water).

What is claimed is:

1. A method for treating peptic ulcer disease in a warm blooded mammal in need of such treatment which comprises orally or parenterally administering to said mammal an anti-peptic ulcer effective amount of a compound of the formula:

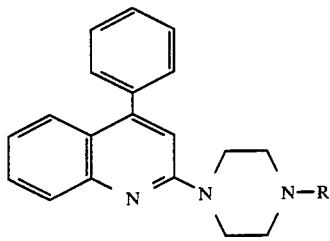

[I]

wherein R is a hydrogen atom or an ethyl group, or a pharmaceutically acceptable salt thereof.

2. The method of claim 1, wherein the active compound is a compound of the formula [I] wherein R is ethyl group.

3. The method of claim 2, wherein the active compound is in the form of dihydrochloride.

4. The method of claim 2, wherein the active compound is in the form of dimaleate.

5. The method of claim 1, wherein the active compound is a compound of the formula [I] wherein R is hydrogen atom.

6. The method of claim 5, wherein the active compound is in the form of monomaleate.

7. The method of claim 1, wherein the active compound is administered in the form of a pharmaceutical preparation for oral or parenteral administration.

8. The method of claim 7, wherein the preparation is administered in oral route.

9. The method of claim 1, wherein the active compound is administered in a dose of 0.01 to 20 mg/kg/day.

10. A method for treating peptic ulcer disease in a warm blooded mammal in need of such treatment which comprises orally administering to said mammal 2-(4-ethyl-1-piperazinyl)-4-phenylquinoline dimaleate in a dose of 0.01 to 20 mg/kg/day.

11. A method for treating peptic ulcer disease in a warm blooded mammal in need of such treatment which comprises orally administering to said mammal 2-(1-piperazinyl)-4-phenylquinoline monomaleate in a dose of 0.01 to 20 mg/kg/day.

* * * * *